United States Patent [19]
Reinhardt et al.

[11] Patent Number: 4,751,343
[45] Date of Patent: Jun. 14, 1988

[54] PROCESS FOR THE PREPARATION OF TERTIARY OLEFINS

[75] Inventors: Horst Reinhardt, Bergheim; Bernhard Schleppinghoff, Dormagen, both of Fed. Rep. of Germany

[73] Assignee: EC Erdolchemie GmbH, Cologne, Fed. Rep. of Germany

[21] Appl. No.: 24,206

[22] Filed: Mar. 10, 1987

[30] Foreign Application Priority Data

Mar. 29, 1986 [DE] Fed. Rep. of Germany ....... 3610704

[51] Int. Cl.$^4$ .............................................. C07C 1/00
[52] U.S. Cl. .................................................... 585/639
[58] Field of Search ......................................... 585/639

[56] References Cited

U.S. PATENT DOCUMENTS 4,447,668 5/1984 Smith et al. ...................... 585/639

FOREIGN PATENT DOCUMENTS 1176620 1/1970 United Kingdom .

Primary Examiner—Curtis R. Davis
Attorney, Agent, or Firm—Sprung Horn Kramer & Woods

[57] ABSTRACT

Tertiary olefins are obtained in pure form by cleavage of the pertinent tert.alkyl ethers with simultaneous formation of the pertinent alcohols on strongly acidic cation exchangers in the H$^+$ form. This cleavage is carried out at elevated temperature and atmospheric to superatmospheric pressure. The process is carried out in such a fashion that the ether to be cleaved is employed as a mixture with water. The water may be employed in an amount from 2–50% by weight, relative to the amount of the ether to be cleaved. Suitable ethers to be cleaved are those based on tertiary $C_4$–$C_7$-olefins and primary $C_1$–$C_4$-alkanols.

15 Claims, 1 Drawing Sheet

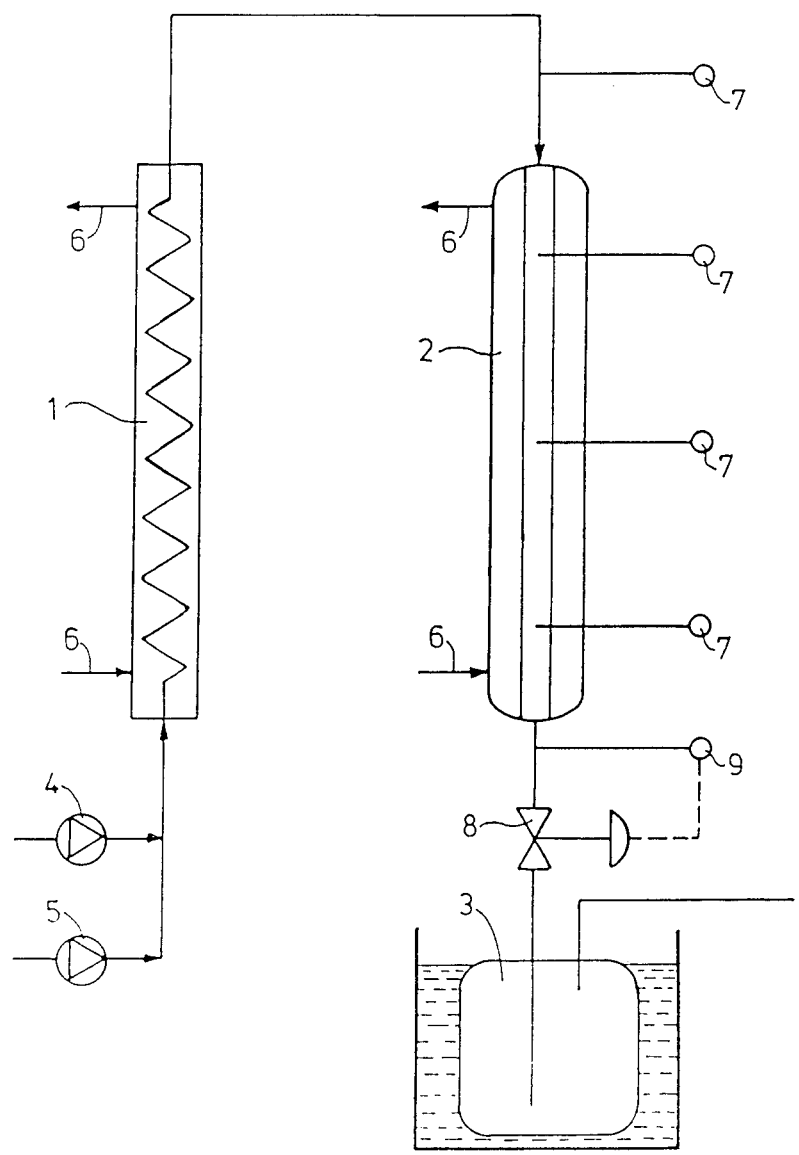

PROCESS FOR THE PREPARATION OF TERTIARY OLEFINS

BACKGROUND OF THE INVENTION

1. Field of the Invention

The invention relates to a process for the preparation of tertiary olefins in pure form by cleavage of the appropriate tert.-alkyl alkyl ethers on strongly acidic cation exchangers in the H+ form.

2. Background Information

Tertiary olefins are important precursors for oligomers, for example, for solvens and lubricants, for polymers and copolymers, and for higher grade chemicals, such as pinacolin, neocarboxylic acids, isoprene and others.

Tertiary olefins are produced in crude form, for example, in the thermal and catalytic cracking of light petroleum, naphtha and other suitable starting materials, or on dehydrogenation and/or isomerization thereof; they usually exist here as a mixture of a large number of saturated and unsaturated attendant materials whose distillative separation is difficult and expensive since it starts from distillation cuts which contain substances of similar boiling point and with the same or a similar number of C atoms. The tertiary olefins are thus generally isolated via selective reaction, separation of the reaction product and decomposition of the separated pure reaction products. Whereas the selective esterification using sulphuric acid and decomposition of the esters formed were used previously, in recent times the selected esterification of the tertiary olefins using alkanols on acidic cation exchangers is preferred in order to avoid using corrosive sulphuric acid. The tert.-alkyl ethers formed may be separated off from the materials accompanying the tertiary olefins by known methods (distillation, azeotropic distillation, extractive distillation, inter alia) and obtained in pure form. The tert.-alkyl alkyl ethers may then be cleaved into the basic tertiary olefins and alkanols; the separation from the alkanols and remaining ether of the tertiary olefins thus prepared presents no difficulties. The cleavage of the ethers is carried out on suitable catalysts at temperatures which are higher than the temperatures required for the formation of the ethers.

Mainly mineral catalysts, such as silicic acids or aluminium oxides having large surface areas, silicoaluminates, mordenites, zeolites, oxides of other elements, phosphoric acid or salts which react in an acidic fashion, were hither-to used as catalysts for the ether cleavage. The mineral catalysts are used at higher temperatures up to 673K. However, undesired by-products, particularly dialkyl ethers, are produced during this from the alkanols produced during the cleavage. This formation of dialkyl ethers increases with increasing temperature and thus removes the basic alkanol, which should be recycled in the overall esterification/ether cleavage process, from the cycle and additionally complicates the work-up. On the other hand, a temperature increase must generally be carried out in order to activate the catalyst sufficiently and in order to achieve sufficient supply of heat for the endothermic ether cleavage. On the other hand, the danger of hydration of the tertiary olefin to be obtained becomes greater due to the water produced during the ether formation, losses of this desired tertiary olefin arising in addition to the losses of alkanol or a downstream hydration necessarily being provided.

In spite of the danger of hydration of the tertiary olefins, the cleavage of ether has been carried out in the presence of water in order to control the undesired formation, occurring primarily, of the dialkyl ethers GB 1,176,620; DE-OS (German Published Specification) 3,142,461). This addition of water also presented itself since the likewise undesired hydration of the tertiary olefins does not yet come to the fore too much at the comparatively high reaction temperatures necessary for the use of the mineral catalysts.

However, acidic cation exchangers in the H+ form have also already been proposed for the cleavage of the tert.-alkyl alkyl ethers (DE-AS (German Published Specification) 1,216,856; U.S. Pat. No. 4,447,668). In this case, reaction temperatures of 333°–393° K. are used. However, the undesired dialkyl ethers can not be avoided as by-products on acid cation exchangers either; further undesired by-products are the oligomers of the tertiary olefins produced. If the reaction temperature is increased in order to increase the conversion of the tert.-alkyl alkyl esters to be cleaved, the formation of the by-products mentioned also increases. On acidic cation exchangers therefore, either relatively low selectivities have been achieved at relatively high temperatures or relatively low conversions have been achieved at relatively low temperatures.

SUMMARY OF THE INVENTION

Surprisingly, it has now been found that the cleavage of tert.-alkyl ethers is also possible in the presence of water, using acidic cation exchangers in the H+ form, without the feared saturation of the cation exchanger with water occurring, which would lead to increased formation of the corresponding tertiary alkanol. The formation of the undesired by-products, namely the dialkyl ether and the oligomers of the tertiary olefins, is suppressed by means of the addition, according to the invention, of water during the cleavage of ether. Furthermore, a large part of the heat of reaction necessary for the endothermic cleavage of ether can be introduced into the reaction space with the aid of the water addition according to the invention. By means of this, the measures which are otherwise necessary for transferring the heat, such as the use of the tube reactors instead of tower reactors, the design of ribs on the inside of the tube, filled with the cation exchanger, or the design of heat-conducting intermediate layers of inert materials (for example, spheres or other shaped elements of steel, $Al_2O_3$ or ceramic) between the cation exchanger layers, if appropriate, as a continuous mixture of cation exchanger and inert material, are effectively supported, simplified or are even rendered completely unnecessary. A still further advantage of the process according to the invention is that it is easier to separate the tertiary olefin produced from the alkanol, which separates in a separate phase together with the water added. Any washing with water of the tertiary olefin obtained which may be necessary is thus considerably simplified; however, in many cases it is completely unnecessary.

Accordingly, a process has been found for the preparation of tertiary olefins by cleavage of the pertinent tert.-alkyl alkyl ethers, with simultaneous formation of the pertinent alkanols, on strongly acidic cation exchangers in the H+ form at elevated temperatures and atmospheric to superatmospheric pressure, which process is characterized in that the tert.-alkyl alkyl ether is employed as a mixture with water.

BRIEF DESCRIPTION OF THE DRAWING

The drawing is a schematic flow diagram of the process according to the present invention.

DETAILED DESCRIPTION OF THE INVENTION

The amount of water to be added according to the invention is, for example, 2–50% by weight, preferably 5–40% by weight, of the amount of the tert.-alkyl alkyl ether employed. In the case of the cleavage of tert.-amyl methyl ether, an amount of 5–20% by weight of water, relative to the amount of the ether, has proven particularly favourable.

In a complete surprising fashion it has even turned out that, in spite of the addition, according to the invention, of water, tertiary alkanol, which formed concomitantly during the preparation of the tert.-alkyl alkyl ethers to be employed according to the invention is partly cleaved back into tertiary olefin and water.

The process according to the invention is carried out at advantageously low reaction temperatures of 333°–400° K., preferably 353°–393° K., at advantageously low pressures, for example 1–50 bar, preferably 1–10 bar, particularly preferably 1–3 bar, and advantageously high WHSV (=Weight Hourly Space Velocity) of 1–50, preferably 2–20, particularly preferably 3–10 kg of ether to be cleaved per hour and per liter of cation exchanger.

In addition, the measures, already mentioned above for improving the heat flow may be used in the process according to the invention. The process according to the invention may be carried out in the gas phase or in the liquid phase, preferably in the gas phase. If the process is carried out in the gas phase, the further advantage arises that the steam introduced into the reactor, if allowed to condense, contributes to the thermal economy of the endothermic cleavage of ether.

According to the invention, high cleavage conversions can be achieved at high selectivity to the desired tertiary olefin, frequently above 99%.

The tertiary olefins and alkanols which can be obtained according to the invention may be separated by distillation or by partial condensation of the alkanols in a fashion which is known in principle. Complete condensation, with formation of two phases, can also be carried out. In all cases, the tertiary olefin which may be obtained during this separation has a reduced alkanol content, compared to other ether cleavage processes, caused by the $H_2O$ addition according to the invention; a proposed phase separation of tertiary olefin and alkanol is carried out faster and more completely.

Any further reduction of the alkanol content in the tertiary olefin which may be necessary can be carried out, for example, using a downstream water washing stage.

Tert.-alkyl alkyl ethers for the process according to the invention are those which are based on primary alcohols having 1–4 C atoms, such as methyl, ethyl, n-propyl or n-butyl, preferably or ethyl, particularly preferably methyl, and tertiary olefins having 4–7 C atoms, such as i-butene, i-amylenes, i-hexenes or i-heptenes, preferably i-butene or i-amylenes.

The following ethers may be mentioned as examples: methyl tert.-butyl ether (MTBE), ethyl tert.-butyl ether, propyl tert.-butyl ether, n-butyl tert.-butyl ether, tert.-amyl methyl ether (TAME), tert.-amyl ethyl ether, tert.-amyl propyl ether, tert.-amyl n-butyl ether, methyl tert.-hexyl ether and methyl tert.-heptyl ether. For the preparation of particular pure tertiary olefins, the tert.-alkyl alkyl ethers mentioned can be distillatively separated off and purified after their formation and before use in the ether cleavage. The cleavage products are the abovementioned basic tertiary olefins and the likewise abovementioned alkanols.

All known types of strongly acidic cation exchangers, such as sulphonated phenol-formaldehyde resins, sulphonated coumarone-indene condensations products, sulphonated polystyrenes, sulphonated styrene-divinylbenzene resins etc. can be employed; they are employed according to the invention in their $H^+$ form.

Sulphonated styrene-divinylbenzene resins, according to the invention, having a degree of crosslinking (divinylbenzene content) of 2–65%, preferably 8–25%, are employed in a preferred fashion.

The use of hitherto not yet published sulphonated styrene-divinylbenzene cation exchangers, modified with $SiO_2$, has proven particularly favourable. Such cation exchangers have an $SiO_2$-content of 0.1–10% by weight, preferably 0.3–3% by weight, relative to the total weight of the $SiO_2$-containing cation exchanger. For the process according to the invention, these $SiO_2$-modified cation exchangers are also employed in the $H^+$ form.

Such $SiO_2$-modified cation exchangers can be prepared, for example, by steeping the cation exchanger in its alkali form in aqueous alkali metal silicate solutions or in aqueous alkylammonium silicate solutions (preferably quarternary alkylammonium silicates) and subsequently precipitating the $SiO_2$ using mineral acid with simultaneous conversion of the cation exchanger into the $H^+$ form.

As alkali form of the cation exchanger, its $Na^+$ or $K^+$ form may be mentioned. Aqueous alkali metal silicate solution, for example sodium or potassium water glass solution or (quarternary) alkylammonium silicate solution, containing 1–20% by weight, preferably 5–15% by weight of alkali metal silicate in the total solution, is added to the water-moist alkali form of the cation exchanger. The duration of action of the water glass solution on the cation exchanger is, for example 1–1,000 hours, preferably 50–200 hours. After this duration of action, the steeped cation exchanger are separated from the excess water glass solution and subsequently treated with dilute mineral acid, such as sulphuric acid, hydrochloric acid, phosphoric acid or nitric acid. The concentration of the mineral acid used is, for example 2–10% by weight.

In the case where the $SiO_2$-contents achieved on single steeping of the cation exchanger in water glass solution or (quarternary) alkylammonium silicate solution are not sufficient, this treatment can be repeated, if appropriate a number of times. The action of the alkali metal/(quarternary) alkylammonium water glass solution usually occurs at temperatures of 293–303 K., but can certainly occur in the temperature range of 283–373 K. The cation exchanger is washed until neutral following the final treatment with mineral acid. It can then be dehydrated using methanol and then, after drying, employed for cleavage of the tert.-alkyl alkyl ethers. However, the cation exchanger may also be employed moistened with methanol, particularly when methanol appears during the ether cleavage. Finally, the cation exchanger, washed neutral, may also be employed water-moist and dried, in the reactor for the ether cleavage, to the H₂O content which is also produced as a result of the addition of H₂O according to the invention.

A variant of the described treatment of the cation exchanger with water glass solution comprises initially allowing the cation exchanger, in the alkali form, to swell in a polar, water-miscible organic solvent and subsequently adding the water glass solution. In a further variant, the swelling of the cation exchanger with the polar, water-miscible organic solvent and the action of the water glass solution may also be carried out simultaneously. Suitable solvents are, for example, polyhydric alcohols, such as glycols and glycerol, acetone, methyl ethyl ketone and others.

The $SiO_2$-modification is preferably carried out using glycols and particularly preferably using monoethylene glycol.

EXAMPLES

EXAMPLE 1 (Preparation of an $SiO_2$-modified cation exchanger)

250 ml of sulphonated styrene-divinylbenzene resin (Lewatit SPC 118 from Bayer), damp with water, were placed in a glass tube of diameter 25 mm and a volume of about 500 ml, having a sealed-in glass frit, and were initially washed with methanol and subsequently with distilled water. The cation exchange resin, pre-purified in this fashion, was subsequently converted into the $Na^+$ form using 5 kg of a 4% strength sodium hydroxide solution, about 2 hours being necessary for this. After separating off the sodium hydroxide solution, the cation exchange resin was transferred into a sealed vessel together with 255 g of a 10% strength aqueous sodium silicate solution (sodium waterglass) and left there for 120 hours at about 25° C. After separating off the sodium silicate solution, the cation exchange resin was rinsed in the glass tube described above together with 250 ml of distilled water, subsequently converted into the $H^+$ form using 750 ml of a 4% strength hydrochloric acid, and washed with distilled water until neutral. The catalyst thus prepared can be employed for the following examples moist with water, moist with methanol or in a dried form. The $SiO_2$ content was 0.46% by weight.

EXAMPLE 2

The following working procedure was carried out for the preparation of an $SiO_2$-modified cation exchanger in the presence of a polar, water-miscible solvent: the cation exchanger used in Example 1 was pretreated as in Example 1 with methanol, distilled water and sodium hydroxide solution. 250 ml of the cation exchanger thus pretreated were transferred into a sealed vessel together with 750 ml of a solution of 375 ml of monoethylene glycol and 375 ml of a 10% strength aqueous sodium silicate solution, and left there for 120 hours. After separating off the cation exchanger, this was rinsed with 250 ml of distilled water in the fashion described in Example 1 and converted into the $H^+$ form using 750 ml of a 4% strength hydrochloric acid, and subsequently washed with distilled water until neutral. This catalyst can also be used moist with water, moist with methanol or in dried form. The $SiO_2$ content was 1.4% by weight.

Examples 3–9

The apparatus depicted in the drawing was used for carrying out the examples. In this drawing, 1 denotes a preheater or evaporator, 2 denotes a cleavage reactor which is filled with a strongly acidic cation exchanger, 3 denotes a cooled and de-aerated receiver, 4 denotes a laboratory pump as metering device for the tert.-alkyl alkyl ether to be cleaved, 5 denotes a laboratory pump as metering device for the water to be added, 6 denotes heat transfer streams, the temperature of which can be adjusted by means of thermostats, 7 denotes temperature measurement points, 8 denotes a pressure valve and 9 denotes a device, for measuring the reaction pressure, which acts on 8 via a control circuit, 2 is a stainless steel twin-jacket reactor having an internal diameter of 25 mm and a length of 350 mm. The reaction mixture condensed in 3 is separated into two phases, which were separated from one another, weighed and analyzed.

The Examples 3–5 are comparison examples (without the addition of water), and Examples 6–9 are examples of the invention (according to the invention, addition of water). In Examples 6 and 7 and in comparison Example 5, an $SiO_2$-modified cation exchanger, employed according to Example 1, was employed, whereas the cation exchanger based on the $SiO_2$-modified cation exchanger prepared in Example 1 (that is to say without this $SiO_2$ modification) was employed in Examples 8 and 9.

The tert.-amyl methyl ethyl ether (TAME) to be cleaved, employed in Examples 3–9, had the following composition:

| | |
|---|---|
| tert.-amyl methyl ether (TAME) | 98.0% by weight |
| tert.-amyl alcohol (TAA) | 0.9% by weight |
| tertiary $C_7$ ethers | 0.5% by weight |
| methanol | 0.1% by weight |
| water | 0.1% by weight |
| benzene | 0.2% by weight |
| other hydrocarbons | 0.2% by weight. |

The following table contains the reaction conditions (pressure, temperature, catalyst, quantity feed) and the composition of the reaction products. Conversion, yield and selectivity were calculated as follows from the percent by weight data of the reaction products:

$$\text{Conversion of } TAME: \frac{A - B}{A} \cdot 100(\%)$$

$$\text{Yield of methylbutenes: } \frac{C \cdot [TAME]}{A \cdot [\text{methylbutene}]} \cdot 100(\%)$$

Selectivity of the $TAME \rightarrow$ methylbutenes reaction $$\frac{C \cdot [TAME]}{(A - B) \cdot [\text{methylbutene}]} \cdot 100(\%)$$

In these formulae:
A = amount of TAME in the starting material
B = amount of TAME in the reaction product
C = amount of methylbutenes generated in the reaction product
[TAME] = molecular weight of TAME
[methylbutene] = molecular weight of the methylbutenes.

The water added to the reaction in Examples 6–9 has not been taken into account in the reaction product data and the calculations carried out; only the amount of water which was already contained in the starting material has been taken into account. When calculating the yield and the selectivity from the compositions, determined analytically, of the reaction products, some values of greater than 100% were computed, showing that part of the TAA present in the starting material was also dehydrated and thus led to a larger amount of methylbutenes than would have been expected from the decomposition of TAME. Only the examples with identical WHSV and identical added amounts of H₂O are suitable for accurate comparison. All the examples and comparison examples specified in the Table were carried out at about 1 bar, a reactor temperature of 363° K. and a temperature of 393° K. of evaporated TAME or TAME/H₂O mixture.

In spite of the addition of H₂O, part of the tert.-amyl alcohol present in the starting material stream was cleaved to form methylbutane, even at relatively high WHSV.

TABLE

Cleavage of tert.-amyl methyl ether (TAME) on sulphonated styrene-divinylbenzene resin (SPC 118) or on the same resin with SiO₂ doping (SPC 118/SiO₂).

| Reaction conditions/examples | 3 | 4 | 5 | 6 | 7 | 8 | 9 |
|---|---|---|---|---|---|---|---|
| Charge of TAME (ml/h) | 300 | 600 | 600 | 300 | 600 | 300 | 600 |
| WHSV* (g/h · ml) | 3.5 | 7 | 7 | 3.5 | 7 | 3.5 | 7 |
| Added amount of H₂O (ml/h) | — | — | — | 20 | 40 | 20 | 40 |
| Catalyst SPC- | 118 | 118 | 118/SiO₂ | 118/SiO₂ | 118/SiO₂ | 118 | 118 |
| Reaction products: all in % by weight | | | | | | | |
| 3-methylbut-1-ene | <0.1 | <0.1 | <0.1 | <0.1 | <0.1 | <0.1 | <0.1 |
| 2-methylbut-1-ene | 7.5 | 7.6 | 8.3 | 10.1 | 9.2 | 10.0 | 9.0 |
| 2-methylbut-2-ene | 51.6 | 48.5 | 52.4 | 59.1 | 55.8 | 58.2 | 55.0 |
| dimethyl ether | 0.1 | 0.1 | 0.1 | <0.1 | <0.1 | 0.1 | <0.1 |
| methanol | 26.3 | 25.4 | 26.8 | 28.0 | 28.4 | 28.1 | 28.5 |
| H₂O | 0.1 | 0.1 | 0.1 | 0.1 | 0.1 | 0.1 | 0.1 |
| TAME | 13.2 | 16.7 | 10.8 | 1.6 | 4.3 | 1.5 | 5.5 |
| C₇ ethers | 0.5 | 0.6 | 0.5 | 0.5 | 0.5 | 0.4 | 0.3 |
| tert.-amyl alcohol | <0.1 | <0.1 | <0.1 | 0.1 | 0.6 | 0.2 | 0.5 |
| C₅ oligomers | 0.1 | <0.1 | <0.1 | <0.1 | <0.1 | 0.4 | <0.1 |
| other hydrocarbons | 0.6 | 1.0 | 1.0 | 0.5 | 1.0 | 1.1 | 1.1 |
| Results: all in % | | | | | | | |
| Conversion | 86.5 | 82.9 | 88.9 | 98.4 | 95.6 | 98.5 | 94.4 |
| Yield  according to the | 87.9 | 83.4 | 90.3 | 102.9 | 96.7 | 101.1 | 95.2 |
| Selectivity  explanations above | 101.6 | 100.5 | 101.4 | 104.6 | 101.1 | 102.7 | 100.8 |

*WHSV = Weight Hourly Space Velocity

It will be appreciated that the instant specification and claimes are set forth by way of illustration and not limitation, and that various modifications and changes may be made without departing from the spirit and scope of the present invention.

What is claimed is:

1. A process for the preparation of a tertiary olefin comprising contacting a tert.-alkyl alkyl ether in admixture with water, on a strongly acidic cation exchanger in the H⁺ form at an elevated temperature of 333° to 400° K. and at atmospheric to superatmospheric pressure, wherein the water is employed in amount from 2-50% by weight of the amount of the tert.-alkyl alkyl ether.

2. A process according to claim 1, wherein the water is employed in an amount from 5-40% by weight of the amount of the tert.-alkyl ether.

3. A process according to claim 1, wherein water is employed in an amount from 5-20% by weight of the amount of the tert.-amyl methyl ether.

4. A process according to claim 1, wherein the tert.-alkyl alkyl ether is prepared by esterification of a tertiary $C_4$-$C_7$-olefin using a primary $C_1$-$C_4$-alkanol.

5. A process according to claim 1, wherein the tert.-alkyl alkyl ester is a tert.-alkyl methyl ether.

6. A process according to claim 1, wherein the ester is selected from the group consisting of methyl tert.-butyl ether, tert.-amyl methyl ether and mixtures thereof.

7. A process according to claim 1, wherein the temperature is 353°-393° K.

8. A process according to claim 1, wherein the pressure is 1-50 bar.

9. A process according to claim 1, wherein the pressure is 1-10 bar.

10. A process according to claim 1, wherein the pressure is 1-3 bar.

11. A process according to claim 1, wherein the process is conducted with a weight hourly space velocity of 1-50 kg of tert.-alkyl alkyl ether per hour and per liter of cation exchanger.

12. A process according to claim 11, wherein the weight hourly space velocity is 2-20.

13. A process according to claim 11, wherein the weight hourly space velocity is 3-10.

14. A process according to claim 1, wherein the process is carried out in the gas phase or liquid phase.

15. A process according to claim 1, wherein the process is carried out in the gas phase.

* * * * *